United States Patent [19]

Tolbert

[11] 4,059,486

[45] Nov. 22, 1977

[54] CELL CULTURE PROCESS

[75] Inventor: William R. Tolbert, Manchester, Mo.

[73] Assignee: Monsanto Company, St. Louis, Mo.

[21] Appl. No.: 738,513

[22] Filed: Nov. 3, 1976

[51] Int. Cl.$^2$ .............................................. C12K 9/00
[52] U.S. Cl. ................................................ 195/1.8
[58] Field of Search ........................................ 195/1.8

[56] References Cited

U.S. PATENT DOCUMENTS 3,850,748  11/1974  Cook et al. ........................ 195/1.8

OTHER PUBLICATIONS

Gottlieb et al.—Fundamental Aspects of Neoplasia (1975), pp. 401–412.
Hammond et al.—Science, vol. 185 (Sept. 13, 1974), pp. 955–957.
Otsuka et al.—J. of Cell Physiology, vol. 85, (1975), pp. 665–674.
Otsuka et al.—J. of Cell Physiology, vol. 87, (1975), pp. 213–220.
Renger et al.—J. of Virology, vol. 11, No. 5 (1973), pp. 702–708.
Gail et al.—Exper. Cell Research, vol. 70, (1972), pp. 33–40.
Ohman et al.—Proc. Nat. Acad. Science, vol. 70, No. 5, (1973), pp. 1569–1573.
Willmer—Cells & Tissues in Culture, vol. 1, (1965), pp. 495 & 496.

*Primary Examiner*—Sam Rosen
*Attorney, Agent, or Firm*—Scott J. Meyer; John D. Upham

[57] ABSTRACT

SV3T3 cells are rapidly propagated in vitro to elaborate MIF and TAF by first growing on a surface and thereafter transferring an inoculum of the growing cells into an agitated liquid suspension of nutrient culture medium, incubating at 30°–38° C while continuing the agitation of the medium, periodically transferring the growing cells into fresh medium and continuing the incubation with agitation of the medium, whereby said cells are proliferated in aggregates and elaborate MIF and TAF in significantly detectable amounts.

10 Claims, 2 Drawing Figures

CELL CULTURE PROCESS

BACKGROUND OF THE INVENTION

This invention relates to suspension cultures of mammalian cells and, more particularly, to the agitated liquid suspension culturing of simian virus 40 transformed 3T3 mouse embryo cells (SV3T3) to produce the physiologically active substances MIF and TAF.

The in vitro viral transformation of cell lines by infecting an established cell line with virus is well known. Thus, the simian vacuolating virus (SV-40) is known to induce the transformation of various cell lines as reported by Black and Rowe, *Proc. Soc. Exptl. Biol. & Med.* 114, 721–27 (1963). The development of the established cell line 3T3 was first disclosed by Todaro and Green, *J. Cell. Biol.* 17, 299–313 (1963) and the transformation of this cell line by SV-40 to alter permanently its properties was further reported by Todaro et al, *Proc. Nat. Acad. Sci.* 51, 66–73 (1964).

The culturing of SV3T3 cells is important for obtaining certain physiologically active products of the cell metabolism. Thus, it is known that these transformed fibroblasts elaborate a macromolecular product that inhibits macrophage migration known as migration inhibition factor (MIF). The nature of MIF produced by sensitized lymphocytes has been fully described by David, *Proc. Natl. Acad. Sci. U.S.* 56, 72–77 (1966) and *Fed. Proceedings,* 30, 1730–35 (1971). The production of MIF from SV3T3 cells in particular is disclosed by Hammond et al, *Science* 185, 955–57 (1974), and by Poste, *Exptl. Cell Res.* 92, 233–90 (1975).

Another substance obtained by the culturing of SV3T3 cells is the tumor angiogenesis factor (TAF) which is known to stimulate the proliferation of new capillaries. The biological characteristics and assay of TAF have been summarized by Folkman, *Cancer Res.* 34, 2109–2113 (1974) and by Folkman and Klagsbrun in Chapter 31 of "Fundamental Aspects of Neoplasia," at pages 401–412, edited by Gottlieb et al, Springer-Verlag, New York, 1975.

The production of both of the aforesaid substances, MIF and TAF, is desired for their respective uses in various investigations of tumor biology and for diagnostic and other medical purposes. Although MIF and TAF can be isolated from tissue grown in vivo, the in vitro production would provide a more adequate and uniform supply of these materials.

The SV3T3 cell is generally known as an adherent anchorage dependent cell; Gail and Boone, *Exptl. Cell. Res.* 70, 33–40 (1972). An anchorage dependent cell when cultured in vitro normally must anchor itself to a surface such as a glass or plastic surface before it can divide. As such, these cells ordinarily are grown as monolayers in vessels such as flasks and petri dishes. While such growth in monolayers often is desirable, an agitated liquid suspension culture of SV3T3 cells would afford significant advantages in growth and harvesting provided that the desired MIF and TAF products would continue to be elaborated by these cultures.

Growth of SV3T3 cells in suspension cultures of 1.2% Methocel (8000 centipoises) has been reported heretofore; Otsuka and Moskowitz, *J. Cell Physiol.* 85, 665–74 and 87, 213–40 (1975). However, these are viscous, unagitated (static) suspensions which do not provide the advantages of cell growth obtained by the agitated liquid suspension culture as defined herein. The nature and characteristics of such static suspension cultures are further described by Stoker et al, *J. Cancer* 3, 683–93 (1968).

BRIEF DESCRIPTION OF THE INVENTION

In accordance with the present invention, a normally anchorage dependent SV3T3 cell line is cultured in vitro in an agitated liquid nutrient medium whereby the cells are propagated in contact with other cells in aggregates of from about 2 to several hundred cells in suspension in the liquid medium. Adaption of the cell line to growth in suspension culture is rapidly obtained within about a two week period. This is unexpected since adaption of other cell lines to suspension culture often takes several months.

The inoculum for the suspension culture is obtained by releasing SV3T3 cells from a conventional surface culture and suspending in an agitated liquid nutrient culture medium and then incubating at a temperature of from about 30° to about 38° C, preferably at about 35° to 37° C. During the two week growth period, the proliferating cells are periodically transferred to fresh media, preferably in culture vessels of progressively increasing size to thereby increase the product volume. At least about two such transfers at predetermined intervals are desired during the two week growth period.

The invention is further illustrated by the accompanying drawing in which:

FIGS. 1 and 2 are photomicrographs of the aggregated cells after 312 hours of agitated liquid suspension culturing.

The rapid growth of the SV3T3 cells in aggregates in accordance with the present invention provides a distinct advantage over the usual suspension culture of cells in which the cell growth comprises essentially cells which attach to the surface of the culture vessel and individual cells which slough off the surface and float in the medium or cells which grow on the surface of soft agar or other gels. Harvesting of the cells grown in aggregates also is simplified in that there is no need to release cells from the vessel surface as required heretofore and the usual difficulties in centrifugation of individual cells in suspension are reduced.

As the cells grow in aggregates in the agitated liquid suspension defined herein, they can be harvested by centrifugation for shorter periods of time and in lower force fields than suspension cultures of cells growing singly. Because of these shorter time periods and lower force fields, less damage than otherwise is done to the cells during this step with a consequent higher percentage yield of viable cells. In comparison to harvesting an equivalent number of cells from monolayer cultures or suspension cultures with cells growing singly, considerable savings in time and labor costs are achieved.

The cell product from the agitated liquid suspension culture medium of this invention has been found to elaborate the desired MIF and TAF as described hereinbefore in significant amounts.

DETAILED DESCRIPTION OF THE INVENTION

Figure 1:
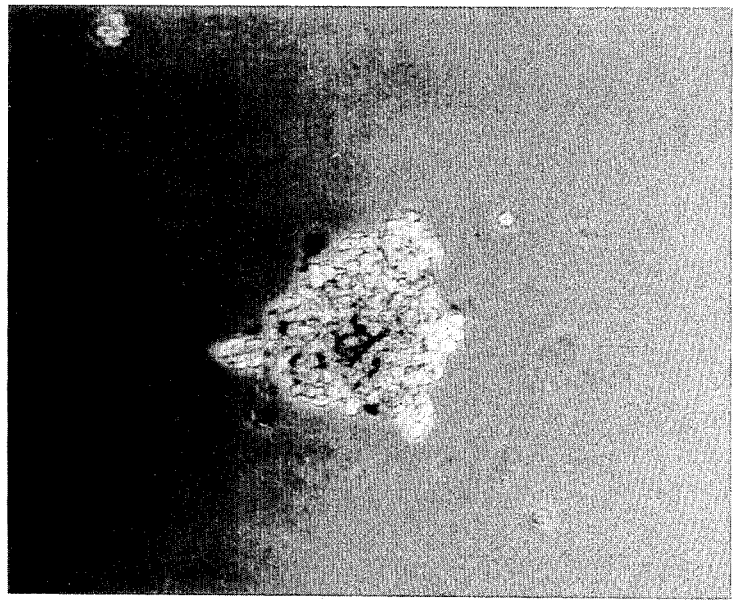

In carrying out the present invention, SV3T3 cells can be initially subcultured by growing to confluency on a surface in monolayers. This can be accomplished, for example, by inoculating a nutrient medium with a seed culture of SV3T3 and growing in conventional 75 cm.$^2$ tissue culture flasks. The seed culture of SV3T3 cells can be, for example, the SV-40 transformed Swiss 3T3 cells which were originally developed from random bred Swiss mouse embryos as reported by Todaro and Green, supra, or the SV-40 transformed BALB/c 3T3 cells which have similar morphology and are otherwise virtually identical to those of SV-40 transformed Swiss 3T3 cells but have been developed from inbred BALB/c mouse embryo cultures as disclosed by Aaronson and Todaro, *J. Cell Physiol.* 72, 141–48 (1968). Cultures of 3T3 cells are available in public depositories, for example, the American Type Culture Collection, Rockland, Maryland, under the code designations ATCC No. CCL 92 and CCl 163.

The nutrient medium for propagation of the SV3T3 cells in the agitated liquid suspension contains assimilable sources of nitrogen, carbon and inorganic salts and can be any of the well-known tissue culture media such as, for example, Basal Medium Eagle's (BME), Eagle's Minimum Essential Medium (MEM), Dulbecco's Modified Eagle Medium, Medium 199, and balanced salt solutions (BSS) such as those of Earle and Hanks fortified with various nutrients. These are commercially available tissue culture media and are described in detail by H. J. Morton, *In Vitro* 6, 89–108 (1970). Use of Dulbecco's Modified Eagle Medium (MEM) is preferred. These conventional culture media contain known essential amino acids, mineral salts, vitamins and carbohydrates. They are also frequently fortified with mammalian sera such as fetal calf serum.

After it has grown to confluency, the foregoing subculture of the SV3T3 cells is transferred to an agitated liquid culture medium of substantially the same components as above. This transfer is carried out by releasing the monolayer of cells from the culture flask and expelling the cells into a rapidly stirred spinner vessel containing the fresh culture medium. The releasing of the cells preferably is carried out by first drawing off or pouring off the spent media, washing the cell layer with phosphate buffered saline, pH about 7 to 7.4, or other such suitable buffer materials having the stated pH, and then trypsinizing the cells to release them from the surface.

Succeeding transfers of the growing cells into fresh media can be made at predetermined or periodic intervals. These transfers can be made into larger size culture vessels containing fresh media as before in order to facilitate the rapid proliferation of cells in large volume.

The suspension culturing can be carried out in glass, plastic or metal vessels. For example, a stainless steel jacketed fermentor of the type manufactured by the New Brunswick Scientific Co. Inc. is generally suitable upon being modified to remove the baffles, as are glass spinner bottles of the type manufactured by Bellco Glass Inc. Illustrative of such fermentors are the devices described in U.S. Pat. Nos. 3,445,341 and 3,445,342. Examples of stirred spinner bottles are those disclosed in U.S. Pat. Nos. 2,958,517 and 3,622,129. Another such apparatus for agitated liquid suspension culturing on a large scale is described in U.S. Pat. No. 3,039,932. The stirring speeds in use of these vessels preferably range from about 200 to about 300 rpm.

Further background information on agitated liquid suspension culture of cells can be obtained by reference to Cherry and Hull, *J. Biochem. Microbiol. Tech. Eng.* II (3), 267–285 (1960), and Moore and Ulrich, *J. Surg. Res.* 5 (6), 270–82 (1965).

Following suitable cell growth, for example, after a 2-week cell culturing period at 35°–37° C, the cells are harvested from the suspension such as by centrifugation at 200–1000 g. The packed cells are then thoroughly washed such as in saline solution, lactated Ringer's solution, phosphate buffered saline, and other such aqueous solutions having a pH of from about 7 to about 7.4.

The washed cells can then be appropriately treated to obtain extracts therefrom which contain the desired MIF and TAF activities. These extracts can be obtained by incubating the cells in saline solution, lactated Ringer's solution or phosphate buffered saline, pH 7 to 7.4, centrifuging and recovering the extract. This extraction is preferably carried out by first resuspending the washed cells in the aqueous buffer or saline with agitation for about 1 to 12 hours at about 4° to 37° C. The cells are then centrifuged and the supernatant is retained as the first extract. The remaining packed cells are then resuspended in an aqueous medium with agitation for about 10 to 30 minutes at about 35° to 37° C. The cells are again centrifuged and the supernatant is retained as the second extract or lysate. The two extracts are each centrifuged at about 9000–10,000 g for about 20 to 30 minutes to remove any residual particulate matter, dialyzed against distilled water to remove salts and other low molecular weight molecules, lyophilized and stored at about −30° C until used.

The bioassay for the TAF activity in the lyophilized material can be carried out in the chorioallantoic membrane (CAM) of the 10- to 11-day old chick embryo as described by Folkman, *Cancer Res.* 34, 2109–13 (1974), 36, 110–14 (1976). According to this procedure, the lyophilized samples to be tested for TAF activity are first dissolved in aqueous phosphate buffered saline and then implanted in the CAM. The intensity of new vascular proliferation converging on the implant is recorded every 24 hours and scored after 5 days on a scale of 1+ to 5+.

The bioassay for the MIF activity in the lyophilized material can be carried out by the standard capillary tube migration inhibition test described by David, *Pathology* 56, 72–77 (1966) and Hammond, *Science* 185, 955–57 (1974). In accordance with this procedure, the lyophilized samples to be tested for MIF activity are admixed with 5% fresh guinea pig serum. This material is then tested against peritoneal exudate cells from guinea pigs placed in capillary tubes and the resulting area of migration is measured by planimetry and compared with control samples.

The following is a further detailed and representative example of the present invention in which 60 liters of cell suspension have been harvested to yield 120 ml. of packed cells within a two week propagation period following the initial inoculation with SV3T3 cells obtained from three 75 cm.$^2$ monolayer flasks. The packed cells have been extracted and found by analysis to elaborate the desired components, MIF and TAF.

In this example, BALB/c SV3T3 cells were grown to confluency in monolayers by incubation at 37° C in flasks containing Dulbecco's Modified Minimum Essential Medium (MEM), containing 4 mg/ml of glucose, supplemented with 10% fetal calf serum.

a. The cells were released from three confluent 75 cm.$^2$ T-flasks using a subculturing procedure as follows:
  i. The expended medium was poured off.
  ii. Phosphate buffered saline solution (PBS), pH 7–7.4, with 0.02% EDTA* was used to rinse the attached cells and then poured off.

Figure 2:
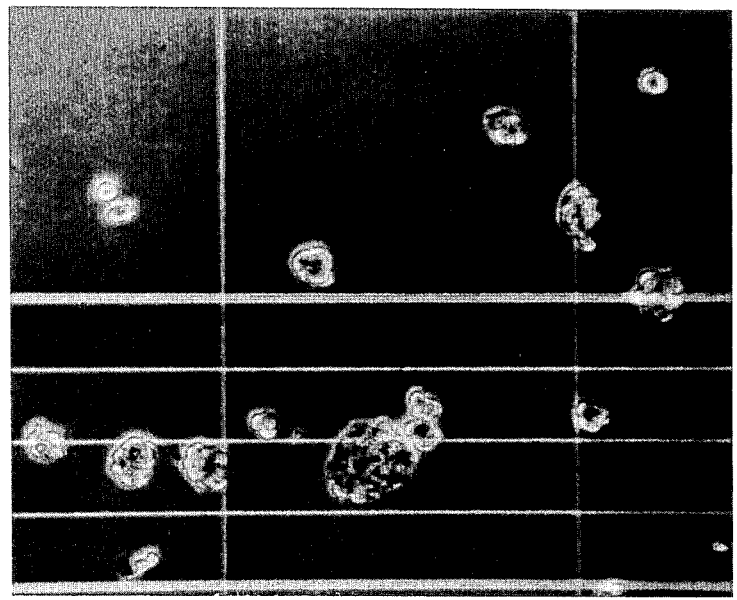

*Disodium salt of ethylenediamine tetraacetic acid iii. Five ml of 0.2% trypsin in PBS with 0.02% EDTA was allowed to stand over the cells at room temperature for 5 min. The flasks were then vigorously shaken to release cells from the surface.

b. The cell suspension in trypsin solution was aspirated 3 to 5 times into a 10 ml pipet and then expelled into a rapidly stirring 500 ml spinner bottle containing Dulbecco's Modified Minimum Essential medium (4 mg/ml glucose) supplemented with 10% fetal calf serum. This spinner was then placed in a 37° C constant temperature room for 72 hrs. with rapid agitation being maintained continuosly. No antibiotics were used at any time during the 2-week cell propagation period in suspension culture of this example.

c. The cell suspension from the 500 ml. spinner bottle was then transferred to a 3-liter spinner bottle which had been modified to permit continuous passage of 5% $CO_2$ in air over the surface of the liquid. The cells were viewed microscopically and appeared to be growing in clumps. Most of the cells were not permeable to the vital dye, trypan blue, thereby indicating their viability. The cells had a granularization of the cytoplasm. Several of the larger clumps had vital dye permeable cells at their center. Fresh medium was added to bring the volume to 3L, and the spinner was stirred rapidly at 37° C for 48 hours.

d. The cells were again viewed microscopically (120 hours since inoculation into the spinner culture) and appeared to be growing in smaller clumps than before with fewer dye permeable cells. The cells still had a granular appearance. An additional one liter of fresh medium was added and the spinner bottle was returned to the 37° C constant temperature room for 48 hours.

e. After 168 hours total, the cell suspension was transferred to a 12L spinner bottle and fresh medium was added to raise the volume to 12L. This bottle was also set up to allow 5% $CO_2$ in air to continually pass over the liquid surface. Five hundred ml of the suspension was retained in a 3L spinner bottle and 3,500 ml of fresh medium was added. The total of 16L of suspension was returned to the 37° C room for 96 hours.

f. After a total of 264 hours in suspension culture, the SV3T3 cells were again examined microscopically. There were very few (less than 5%) dye permeable cells and the cellular cytoplasm had lost its granular appearance. The cells were growing in clumps up to 0.02 mm in diameter while smaller aggregates of 2, 3, 4 or more cells were also visible. The 3L spinner cell suspension was transferred to a 12L spinner bottle with addition of fresh medium. The 12L spinner cell suspension was split into 4 new 12L spinners with the addition of fresh medium. All of these were set up with 5% $CO_2$ in air. In addition, a 1L non-gassed spinner bottle and a 3L gassed spinner bottle were used to maintain the culture. All spinner bottles were returned to the 37° C room for 72 hours.

g. One of the 12L spinner bottles had samples removed every 24 hours for DNA determinations (see the table below) and 1L of the cell suspension was removed and the cells were frozen in liquid $N_2$. FIGS. 1 and 2 show photomicrographs made of the suspension culture of cells at 312 hours after initiation of the culture in suspension, taken at about 30X magnification. In particular, FIG. 1 shows a relatively large clump of cells while FIG. 2 shows several smaller clumps of cells in a hemacytometer chamber.

h. After 336 hours in suspension culture, 60L of suspension were harvested to yield 120 ml of packed cells ($8.1 \pm 0.22 \times 10^{10}$ cells by DNA determination) which were extracted for biologically active components.

Suspension cultures, 3L gassed and 1L non-gassed, have been maintained for periods in excess of 2 months with removal of cells and addition of fresh medium periodically.

i. The cells in the foregoing example were harvested by centrifugation at 200-1000 g and the packed cells were then washed successively three times in PBS, pH 7-7.4.

| Growth by SV3T3 Cells in Suspension by DNA Determination | | |
|---|---|---|
| Time* in hours | μg DNA per ml | Cell number** per ml × $10^{-6}$ |
| 2 | 3.56 ± 0.14 | 0.37 ± 0.015 |
| 24 | 7.48 ± 0.45 | 0.778 ± 0.047 |
| 48 | 11.04 ± 0.39 | 1.15 ± 0.041 |
| 72 | 15.2 ± 1.65 | 1.58 ± 0.17 |

*Time since inoculation of cells into 12L spinner from which 25 ml. samples were removed. This spinner was inoculated 264 hours after initiation of SV3T3 cells in suspension.
**Cell number estimated as 9.61 μg DNA per $10^6$ SV3T3 cells expressed as ± standard deviation.

In order to further substantiate the successful proliferation of SV3T3 cells in the agitated liquid suspension culture, a portion of said cells were returned to stationary tissue culture flasks for growth in monolayers. After reaching confluency, the cells were placed in an agitated liquid suspension culture as before and again were found to proliferate rapidly in aggregates.

Still further confirmation of the foregoing cell growth results was obtained by the fluorescent antibody technique of Coons. By this technique, known fluorescence labeled antibodies to SV3T3 cells were used to demonstrate the presence of antigen in the SV3T3 cells grown in the foregoing suspension cultures.

MIF and TAF activities in the cell product harvested from the foregoing agitated liquid suspension culture are demonstrated as follows:

The washed cells are resuspended in PBS, pH 7-7.4, to a concentration of about $5 \times 10^6$ $5 \times 10^8$ cells per ml. The cell suspension is then stirred at 4° C for 4 hours and again centrifuged. The supernatant is retained as the first extract. The remaining packed cells are then resuspended at 37° C in distilled water to a concentration of about $5 \times 10^6$ to $2 \times 10^7$ cells per ml and stirred for about 20 minutes. The suspension is again centrifuged and the supernatant is retained as the second extract or lysate. The two extracts are further centrifuged at 9000 g in a Sorvall RC2 B centrifuge for about 30 minutes, dialyzed against distilled water at 4° C for 4-8 hours, and then frozen and lyophilized. The MIF activity in the lyophilized extract is determined by the capillary tube migration inhibition test and the TAF activity in the lyophilized extract is determined by the chorioallantoic membrane test described hereinbefore.

While in the foregoing the suspension culture of SV3T3 cells is described with particular reference to the production of MIF and TAF, it will be appreciated that the invention is not limited to the production of these specific factors. Other factors, especially proteinaceous substances, and various desired metabolites can be extracted from the cells and the spent culture fluid.

Various other examples will be apparent to the person skilled in the art after reading the disclosure herein without departing from the spirit and scope of the invention and it is intended that all such further examples be included within the scope of the appended claims.

What is claimed is:

1. A method of rapidly propagating SV3T3 cells in vitro to elaborate MIF and TAF comprising growing SV3T3 cells on a surface, thereafter transferring an inoculum of said growing cells into a normally liquid suspension of nutrient culture medium of known essential amino acids, mineral salts, vitamins, and carbohydrates, incubating at a temperature of from about 30° to about 38° C while substantially continuously maintaining agitation of said medium, periodically transferring the growing cells into fresh nutrient culture medium and continuing the agitated incubation until harvest whereby said cells are proliferated in aggregates and elaborate MIF and TAF in significantly detectable amounts.

2. The method of claim 1 in which the nutrient culture medium is Dulbecco's Modified Minimum Essential medium.

3. The method of claim 1 in which the incubation temperature is from about 35° to about 37° C.

4. The method of claim 1 in which two periodic transfers of the growing cells into fresh nutrient culture medium are made at predetermined intervals.

5. The method of claim 1 in which the nutrient culture medium is fortified with mammalian serum.

6. The method of claim 5 in which the mammalian serum is fetal calf serum.

7. The method of claim 1 in which the SV3T3 cells are BALB/c SV3T3 cells.

8. The method of claim 1 in which the SV3T3 cells are BALB/c SV3T3 cells, the nutrient culture medium is Dulbecco's Modified Minimum Essential medium fortified with fetal calf serum, the incubation temperature is from about 35° to about 37° C and two periodic transfers of the growing cells into fresh nutrient culture medium are made at predetermined intervals.

9. The method of claim 1 including the additional step of harvesting the cells and extracting therefrom an active concentrate of MIF.

10. The method of claim 1 including the additional step of harvesting the cells and extracting therefrom an active concentrate of TAF.

* * * * *